US006867308B2

(12) United States Patent
Bartok et al.

(10) Patent No.: US 6,867,308 B2
(45) Date of Patent: Mar. 15, 2005

(54) PROCESS FOR SEPARATION OF TOCOPHEROLS

(75) Inventors: Laslow Bartok, Decatur, IL (US); Ahmad Hilaly, Springfield, IL (US); Christine M. Schuette, Decatur, IL (US); Rishi Shukla, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 10/246,760

(22) Filed: Sep. 19, 2002

(65) Prior Publication Data

US 2003/0153616 A1 Aug. 14, 2003

Related U.S. Application Data

(60) Provisional application No. 60/323,228, filed on Sep. 19, 2001.

(51) Int. Cl.[7] .............................................. C07D 311/72
(52) U.S. Cl. ..................................... 549/413; 549/398
(58) Field of Search ................................. 549/413, 398

(56) References Cited

U.S. PATENT DOCUMENTS

| | | | |
|---|---|---|---|
| 3,122,565 A | 2/1964 | Kijima et al. | |
| 3,402,182 A | 9/1968 | Kijima et al. | |
| 4,122,094 A | 10/1978 | Woziwodzki | |
| 4,217,285 A | * 8/1980 | Yoshino et al. | 549/411 |
| 4,480,108 A | 10/1984 | Foster | |
| 4,594,437 A | 6/1986 | Sampathkumar | |
| 4,602,098 A | 7/1986 | Foster | |
| 4,607,111 A | 8/1986 | Foster | |
| 4,645,845 A | 2/1987 | Gehrken et al. | |
| 4,914,217 A | * 4/1990 | Chan et al. | 549/398 |
| 5,157,132 A | 10/1992 | Tan et al. | |
| 5,428,052 A | * 6/1995 | Shroot et al. | 514/415 |
| 5,487,817 A | * 1/1996 | Fizet | 203/38 |
| 5,504,220 A | 4/1996 | Kuo et al. | |
| 5,512,691 A | 4/1996 | Barnicki et al. | |
| 5,786,491 A | 7/1998 | Hamlin et al. | |
| 5,821,264 A | * 10/1998 | Lane et al. | 514/458 |
| 2002/0042527 A1 | 4/2002 | Summer, Jr. | |
| 2002/0142083 A1 | 10/2002 | Jacobs | |

FOREIGN PATENT DOCUMENTS

| | | |
|---|---|---|
| EP | 0 171 009 A2 | 2/1986 |
| EP | 1 083 174 A1 | 3/2001 |
| JP | 60-48981 | 3/1985 |
| JP | 60-149582 | 8/1985 |
| WO | WO 97/07113 A1 | 2/1997 |
| WO | WO 98/24779 A1 | 6/1998 |
| WO | WO 99/38859 A1 | 8/1999 |
| WO | WO 99/38860 A1 | 8/1999 |
| WO | WO 00/43095 A2 | 7/2000 |
| WO | WO 00/43095 A3 | 9/2000 |
| WO | WO 02/50054 A2 | 6/2002 |

OTHER PUBLICATIONS

Abidi, S.L., "Chromatographic analysis of tocol–derived lipid antioxidants," *J. Chrom. A.* 881:197–216, Elsevier Science B.V. (Jun. 2000).

Bro–Rasmussen, F., and Hjarde, W., "Determination of α–Tocopherol by Chromatography on Secondary Magnesiun Phosphate," *Acta Chem. Scand.* 11:34–43, Munksgaard (1957).

Dicks–Bushnell, M.W., "Column Chromatography in the Determination of Tocopherol: Florisil, Silicic Acid, and Secondary Magnesium Phosphate," *J. Chromatog.* 27:96–103, Elsevier Science (1967).

Qureshi, A.A., et al., "Isolation and Identification of Novel Tocotrienols from Rice Bran with Hypocholesterolemic, Antioxidant, and Antitumor Properties," *J. Agric. Food Chem.* 48:3130–3140, American Chemical Society (Aug. 2000).

Shin, T. –S., and Godber, J.S., "Isolation of four tocopherols and four tocotrienols from a variety of natural sources by semi–preparative high–performance liquid chromatography," *J. Chromatogr. A.* 678:49–58, Elsevier Science B.V. (1994).

Dialog File 351, Accession No. 4275894, Derwent WPI English language abstract for Japanese Patent Publication No. JP 60–48981, Derwent Information Ltd. (1985).

Dialog File 351, Accession No. 4405616, Derwent WPI English language abstract for Japanese Patent Publication No. JP 60–149582, Derwent Information Ltd. (1985).

Pending Non–Provisional U.S. Appl. No. 10/285,700, Binder et al., filed Nov. 1, 2002 (Not Published).

* cited by examiner

*Primary Examiner*—Cecilia J. Tsang
*Assistant Examiner*—Raymond Covington
(74) *Attorney, Agent, or Firm*—Kirkpatrick & Lockhart; Nicholson Graham LLP

(57) ABSTRACT

A process for separation of specific tocopherols from a mixture of tocopherols is disclosed. The process includes methods of separation of the tocopherols from residues of vegetable oil refining and other various food sources by dissolving in organic solvents and eluting over non-ionic adsorbent resins.

10 Claims, No Drawings

PROCESS FOR SEPARATION OF TOCOPHEROLS

CROSS-REFERENCE TO RELATED APPLICATION

The present application claims the benefit of the filing date of U.S. Provisional Application No. 60/323,228, filed Sep. 19, 2001, which is incorporated herein by reference in its entirety.

BACKGROUND OF THE INVENTION

Field of the Invention

This invention relates to a process for separation of specific tocopherols from a mixture of tocopherols.

Vitamin E is the most important fat-soluble antioxidant. It is synthesized only in plants and is a very important dietary nutrient for humans and animals. Tocopherols are present in oil seeds, leaves and other green parts of higher plants. The term vitamin E is now considered to be the generic name describing both the tocopherols and tocotrienols. Tocopherols and tocotrienols are distinguished by their side chains. While tocopherols have a saturated phytyl tail, tocotrienols possess an unsaturated isoprenoid side chain. Tocopherols and tocotrienols are further separated into individual compounds assigned by the Greek letter prefixes ($\alpha$, $\beta$, $\delta$, $\gamma$) depending on the number and position of methyl substitution on the chromanol ring. In many foods, alpha- and gamma-tocopherol accounts for most of the vitamin E activity. While tocopherols are generally present in common vegetable oils (i.e. soy, canola, wheat germ, sunflower), tocotrienols are concentrated in cereal grains (i.e. oat, barley, and rye, rice bran), with the highest level found in crude palm oil. The antioxidant activity of tocopherols and tocotrienols is primarily attributed to their ability to donate their phenolic hydrogens to lipid free radicals (Karnal-Eldin & Appelqvist, *Lipids* 31:671–701 (1996)). The primary form of vitamin E in dietary and animal feed supplements is $\alpha$-tocopherol. However, it is widely known that $\gamma$-tocopherol is the major form present in our diet.

It has been discovered that the individual members in the class of tocopherols exhibit different biological properties from one another and play different roles in cells. It has been reported that $\gamma$-tocopherols may be involved in the pathogenesis of prostate cancer. Similar reports have also been published on its use in the treatment of natriuretic disease (U.S. Pat. Nos. 6,048,891; 6,242,479). Numerous other studies recently have promoted the benefits of $\gamma$-tocopherols for human diet. Helzlsouer et al. (*J Natl. Cancer Inst.* 92:2018-2-023 (2000)) report on the possible association between $\gamma$-tocopherol and prostate cancer. Recent evidence also indicates that $\gamma$-tocopherol is a superior trapping agent for electrophilic species, like nitrogen oxides or NO, (Christen et al., *Proc. Nad. Acad. Sci. USA* 94:3217–3222 (1997)). Similarly it has been shown that $\gamma$-tocopherol has the unique ability to inhibit oxidative damage caused by reactive nitrogen species such as peroxynitrite (Papas A. M., Antioxidant Status, Diet Nutrition and Health (1999)). Vitamin E has been promoted as an antioxidant with a unique structure. Due to its ability to neutralize free radicals it has been shown to prevent a chronic disease, slow down aging, help maintain good cardiovascular health and is associated with a reduced risk of prostrate and other cancers. However, these reports have been debated.

Presently only $\alpha$-tocopherol is available commercially as an individual compound from a synthetic source. However, recent studies have shown the importance of other forms of vitamin E, notably $\gamma$-tocopherol. Other forms of vitamin E, derived from natural sources contain mixtures of $\alpha$, $\beta$, $\delta$, and $\gamma$ tocopherols. Hence there is a need for making enriched or purified $\gamma$-tocopherols from natural or synthetic sources.

Numerous processes have been used for separating and isolating various tocopherol homologues. These have included esterification, saponification, extraction, ion exchange, adsorption chromatography, short path distillation, crystallization and high performance liquid chromatography. U.S. Pat. Nos. 4,480,108; 4,602,098 and 4,607,111 describe a process for selective deacylation of tocopherol esters followed by separation of esters from the free tocopherols. Tocopherols can also be removed by a series of distillations. U.S. Pat. Nos. 5,512,691; 5,660,691 and 5,487,817 describe steps to obtain a tocopherol containing concentrate by selective esterification of sterols followed by a series of distillation steps. U.S. Pat. No. 4,122,094 describe methods of separating the mixtures of $\alpha$, $\beta$, $\delta$ and $\gamma$ tocopherols using liquid/solid chromatography techniques. However this patent describes a method of separation using high performance liquid chromatography which uses chloroform as the liquid phase. This technique cannot be scaled up commercially and there are obvious difficulties associated with using chlorinated solvents on an industrial scale. U.S. Pat. Nos. 3,122,565 and 3,402,182 have described processes using strong base anion resins for separating tocopherols and refining tocopherol homologues. However, these processes require large volumes of solvent, an acidic elution step and caustic regeneration of the resin after each cycle. This process was able to isolate high purity fractions of tocopherols. Elution with methanol acetic acid was found to be optimal in this process. U.S. Pat. No. 5,487,817, in examples 4–6, describes separation of tocopherols on an ion exchange resin using a combination of isopropanol and acid methanol. U.S. Pat. No. 4,217,285 describes a process for manufacture of high purity $\alpha$-tocopherol by condensing trimethylhydroquinone and a phytol in the presence of catalyst and silica gel. EP 10833174 describes a method for producing purified tocotrienols and tocopherols using liquid chromatography where the stationary phase is silica and the mobile phase consists of alcohol and water. U.S. Pat. No. 4,595,437 describes a process for separation of tocopherols by urea complex formation, and EP 0171009 describes liquid/liquid extraction with caustic methanol to produce an enriched fraction of tocopherols. Similar processes have also been described in two applications, WO 99/38859 and WO 99/38860. Lastly JP6004898 and JP60149582 describes processes to concentrate tocopherols using supercritical carbon dioxide.

None of the processes described in the literature address a method for producing enriched fractions of $\gamma$-tocopherol that can be performed economically. Thus, it would be desirable to have a method for isolating increased quantities of $\gamma$-tocopherol. The prior art methods for increasing the concentration of $\gamma$-tocopherol are inefficient for the production of the product. The present invention describes methods for production of enriched fractions of tocopherols from natural or synthetic sources of a tocopherol containing mixture.

BRIEF SUMMARY OF THE INVENTION

The present invention is directed to a method for producing a purified tocopherol product, principally $\gamma$-tocopherol (2,7,8-trimethyl-2-(4',8',12'-trimethyltridecyl)-6-chromanol), from a mixed tocopherol source which may be natural or synthetic. The structure of the respective homologues is given below:

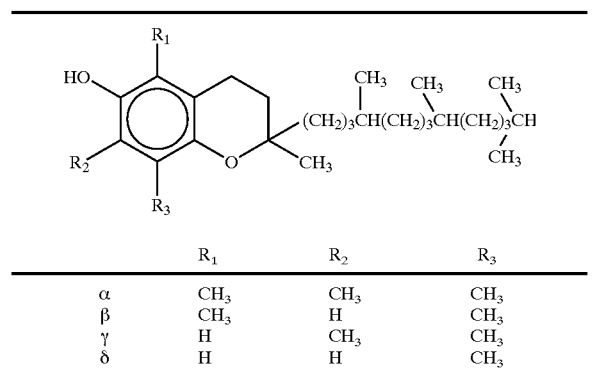

| | $R_1$ | $R_2$ | $R_3$ |
|---|---|---|---|
| α | $CH_3$ | $CH_3$ | $CH_3$ |
| β | $CH_3$ | H | $CH_3$ |
| γ | H | $CH_3$ | $CH_3$ |
| δ | H | H | $CH_3$ |

A further object of this invention is to provide a process for separating the α, β, γ, and δ-tocopherols from residues of vegetable oil refining. A further object of this invention is to provide a means for separating the aforementioned mixtures from various food sources. Another object of the present invention is to prepare a product containing high levels of γ-tocopherols where the amount of α-tocopherol is less than 3% by weight.

The feed material for the present process is derived from sources, including but not limited to residues from vegetable oil refining, vegetable oil sources, tocopherol concentrates and tocopherol mixtures of low purity. The tocopherol containing oil products are dissolved in a solvent according to their solubility in the solvent and the loading capacity of the resin used. Typical concentrations of tocopherols in the range of 5% to 75% oil in the solvent may be practiced. The optimum range is determined by the total tocopherol concentration in the solvent, type of solvent and type of resin used. It is known that various tocopherol homologues exhibit different acidities in weakly self-dissociating solvents which can act as a proton donors (U.S. Pat. No. 3,402,182).

The method of the present invention involves passing a solution of a tocopherol homologue mixture in a polar solvent mixed with another polar solvent (such as methanol and a ketone like acetone, for example) through a strong basic anion exchange resin column immersed in said polar solvent and further passing the polar solvent through the resin, thereby first eluting the most non polar tocopherol (α-tocopherol) followed by fractions enriched with δ-tocopherol. The most polar of the tocopherols is finally eluted with a solution containing high concentrations of a ketone and another polar solvent such as an alcohol. By removing the solvent from the respective fractions under low temperature and high vacuum, the respective tocopherol homologues having high purity can be isolated.

In another embodiment of this invention, a non-ionic adsorbent resin is loaded with a solution of a tocopherol homologue mixture in a long chain alkane solvent. By further passing the long chain alkane solvent over the resin, the non polar α-tocopherol is eluted. By adding a small amount of a ketone, the polarity of the elution solvent is modified to suit the desorption of γ-tocopherol. This is followed by further elution with a highly polar solvent that removes all of the residual tocopherols adsorbed on to the resin. By removing solvent from the respective fractions under low temperature and high vacuum, respective homologues having high purity can be isolated. This may be accomplished by initially removing solvent from the fractions by distillation under 0.1–10.0 mm Hg at temperatures between 100–180° F. followed by high-vacuum, short path distillation carried out in manners conventional in the art. High vacuum short path distillation is performed at pressures between 0.001 mm Hg and 1 mm Hg and temperatures between 250–500° F., preferably at 0.039 mm Hg and 400° F. This process results in product fractions, which contain individual tocopherols of high purity.

The chromatographic separation is commonly carried out at room temperature. The preferred range of temperatures is between −20° C. and the boiling point of the solvent. However a more preferred range is between 10° C. and 40° C.

According to the embodiments of this invention, the difficult elution steps with acidic solvents and the necessary regeneration with caustic solvents, which have characterized the methods known and used earlier, are eliminated. This allows the present invention to be practiced at a low cost.

Strong basic anion resins and non-ionic adsorbent resins can be used in the present invention depending, as those of skill in the art will recognize, on the combination of solvents used. Strongly basic anion exchange resins are divided into two groups Type I resins and Type II resins, and both of them effectively adsorb the free tocopherol material. Similarly non-ionic adsorbents such as silica gels may be used very effectively to isolate fractions very high in respective tocopherol homologues.

Any commercially available or prototype strong/weak base anion exchange resins or non-Ionic adsorbent resins may be effectively employed in performing the embodiments of this invention. Examples of such resins include Dowex 1X2-100, 1X2-200, 2X8-100, MARMSA, MSA2, XUS 40283, XUS 40285, (Dow Chemical Co.); Diaion PA406, PA408, PA412, PA416, PA418, HPA75 (Mitsubishi Chemical America Inc.); Amberlite IRA-900, IRA-910, IRA-400 (Rohm and Hass); C-560, C18-C560, C8-C560 (Uetikon): S100, S300 (Silicycle); Amberlyst A15, Amberlyst A21, Amberlyst A26, XAD4, XAD16 (Rohm and Hass); ADS 400, ADS 600, A2XMP (Thermax Inc.) and S75, S150, BI 6311, Exmere Silica Gel 60 Å (YMC). The strong base anion resins are usually sold as chlorine type. Consequently, prior to operation for the tocopherol purification according to the process of the present invention, the resins are treated with an aqueous solution of 1N–2N alkali hydroxide solution in order to convert the resin to a hydroxyl (—OH) type. This is followed by washing with water and finally replacement with the polar solvent, which may or may not act as a proton donor. The non-ionic silica based resins do not need conversion into OH form as they purify the tocopherols based on polarity of solvent and adsorption of the tocopherol oil on to the resin.

The first polar solvent used in the strong base anion resin may be a low carbon alcohol, preferably methanol or isopropanol. Higher alcohols may also be utilized. The long chain alkane used in the non-ionic resin may include, but is not limited to, hexane, heptane, octane, or any other long chain alkane which is relatively non polar and in liquid form under temperatures similar to those described herein. In order to change the polarity of the eluting solvent, a mixture with a ketone is used which may include, but is not limited to, acetone, 2-butanone, 2-pentanone, cyclopentanone, 4-methyl-2-pentanone, 2-heptanone, 3-heptanone, 4-heptanone, 4-hydroxy-4-methyl-2-pentanone or 4-methyl-3-penten-2-one. The polar solvent described in the embodiments of this invention may also be monohydric alcohol. Any alcohol containing one to six carbon atoms may be employed such as, for example, methyl alcohol, ethyl alcohol, isopropyl alcohol, n-propyl alcohol, isoamyl alcohol, n-amyl alcohol, hexyl alcohol, butyl alcohol, isobutyl alcohol and similar monohydric alcohols. Monohydric alcohols having one to four carbon atoms are also preferred. Mixtures of monohydric alcohols with other polar solvents and solubility may also be used. Some examples of these mixtures may be methyl alcohol-ethyl alcohol, methyl alcohol-butyl alcohol, ethyl alcohol-isopropyl alcohol, methyl alcohol-pyridine, methyl alcohol-acetonitrile, methyl alcohol-acetone, ethyl alcohol-acetone, methyl alcohol-2-butanone, ethyl alcohol-2-butanone, etc. These mixtures can also be employed as solvents for separation of tocopherols on the strong base anion resins in order to increase the loading of tocopherols on the resin and improve resolution of the tocopherol.

It is important to use the strong base anion resins in OH form, as little adsorption is observed when the resin used is in Cl— or other forms. Similarly, using pure non-polar solvents, such as alkanes, on the strong base anion resins does not result in any separation of the homologues. It is an important feature of this invention that repeated elution with acidic solvents followed by caustic regeneration of the resin is completely avoided. Hence, this process is easier to implement on a large scale than currently known processes. The present invention is applicable to many sources of feed material namely natural glyceride oils, deodorizer sludge and products derived from vegetable oil refining, partially concentrated tocopherol products, synthetically and semi synthetically prepared tocopherol products and mixed tocopherol concentrates.

Natural tocopherol sources are known to contain free fatty acids and these have been known to interfere with the separation of tocopherols by the chromatographic resins. Consequently, it is important to lower the acid value of the feed material to less than 10, more preferably to 3 or less. Even more preferably, lower the acid value of the feed material to less than 1. The feed material is purified substantially to remove all other constituents of natural source materials such as sterols, sterol esters, glycerin, hydrocarbons, waxes, higher alcohols, pigments and polymerized organic substances, squalene methyl esters and other constituents which might interfere with the chromatographic separation process described according to this invention.

Mixed tocopherol concentrates and semi-synthetically prepared tocopherol concentrates can be purified according to this invention followed by further purification with well-known techniques such as molecular distillation, solvent extraction, crystallization or combinations thereof.

Additional advantages of the invention will be set forth in part in the examples which follow, and in part in the description of the invention, or may be learned from practice of the invention. The advantages of the invention will be realized and attained by means of the elements and combinations particularly pointed out in the appended claims. It is to be understood that both the foregoing general description and the following examples are exemplary and explanatory only and are not restrictive of the invention as claimed.

DETAILED DESCRIPTION OF THE INVENTION

EXAMPLE 1

This example illustrates the separation of tocopherol homologues utilizing Silica Gel.
Preparation of Resin and Feed Material A sample of commercially available non-wintered concentrated mixed tocopherols was obtained from ADM Nutraceuticals, a division of Archer Daniels Midland Company, Decatur, Ill. The specifications of the product are given below:
d-α tocopherol 88.4 g/kg
d-β tocopherol 13.6 g/kg
d-γ tocopherol 602.8 g/kg
d-δ tocopherol 202.1 g/kg Total tocopherols: 906.9 g/kg
Acid value 0.9
Gardner color 8.20
Specific Rotation 39°

Feed material for chromatographic separation using Silica Gel was prepared by dissolving 251.14 g mixed tocopherol concentrate in 750 ml heptane (FEED A). A glass liquid-chromatography column (2.54 cm I.D.) was slurry packed in heptane with Uetikon AG C-560 silica gel obtained form CU Chemie Uetikon GmbH (Princeton, N.J.). Characteristics of the gel are given below.
$SiO_2$: 99.5%
Bulk Density 485 g/l
Specific surface area 500 $m^2$/g
Nominal pore diameter 60 Å
Pore volume 0.8 ml/g
Water content 2–4%

The resin was cleaned with 500 ml of HPLC grade heptane. The resin was then back flushed with heptane until the resin bed volume expanded by about one-half of its original packed volume in order to partition the resin by size. The final packed volume was 100 ml. The resin was then flushed with 10 bed volumes (BV) of heptane to remove all traces of water.

50 ml of FEED A was loaded on the resin column by gravity flow and the following fractions were eluted. Acetone fractions represent solutions of acetone in heptane.

| Tocopherols (%) | Alpha | Beta | Gamma | Delta | Yield (%) |
| --- | --- | --- | --- | --- | --- |
| Raffinate | | | | | 0.00 |
| 500 ml Heptane | 76.1 | 0.4 | 19.4 | 4.1 | 8.12 |
| 250 ml 5% Acetone 95% Heptane | | | | | 0.00 |
| 250 ml 5% Acetone 95% Heptane | 5.2 | 1.7 | 75.9 | 17.2 | 61.71 |
| 250 ml 5% Acetone 95% Heptane | 0.5 | 0.2 | 27.7 | 71.5 | 12.49 |
| 250 ml 5% Acetone 95% Heptane | 1.0 | 0.3 | 12.3 | 86.5 | 5.14 |
| 500 ml 70% Acetone 30% Heptane | 8.0 | 0.0 | 22.0 | 70.0 | 4.60 |
| 500 ml Heptane | COLUMN REGENERATION | | | | |

Hence by selective elution of the column we were able to isolate fractions with γ-tocopherol content of 75.9% with 61.71% yield.

EXAMPLE 2

This example illustrates the effect of change in acetone concentration in elution of the product. 50 ml of FEED A was loaded on to the column by gravity flow as described in Example 1.

| Tocopherols (%) | Alpha | Beta | Gamma | Delta | Yield (%) |
| --- | --- | --- | --- | --- | --- |
| Raffinate | | | | | 0.00 |
| 500 ml Heptane | 76.5 | 1.3 | 22.0 | 0.1 | 10.10 |
| 250 ml 7% Acetone 93% Heptane | | | | | 0.00 |
| 250 ml 7% Acetone 93% Heptane | 4.5 | 1.6 | 74.5 | 19.5 | 61.89 |
| 250 ml 7% Acetone 93% Heptane | 1.7 | 0.6 | 37.6 | 60.1 | 12.72 |
| 250 ml 7% Acetone 93% Heptane | 1.7 | 0.7 | 37.2 | 60.3 | 5.56 |

-continued

| Tocopherols (%) | Alpha | Beta | Gamma | Delta | Yield (%) |
|---|---|---|---|---|---|
| 500 ml 70% Acetone 30% Heptane | 11.3 | 1.3 | 19.9 | 67.5 | 4.72 |
| 500 ml Heptane | COLUMN REGENERATION | | | | |

Hence by selective elution of the column we were able to isolate fractions with γ-tocopherol content of 74.5% with 61.89% yield.

EXAMPLE 3

This example illustrates the effect of change in acetone concentration from levels used in commercial applications in elution of the product. 50 ml of FEED A was loaded onto the column by gravity flow as described in Example 1.

| Tocopherols (%) | Alpha | Beta | Gamma | Delta | Yield (%) |
|---|---|---|---|---|---|
| Raffinate | | | | | 0.00 |
| 500 ml Heptane | 76.1 | 0.4 | 19.4 | 4.1 | 8.12 |
| 250 ml 3% Acetone 97% Heptane | | | | | 0.00 |
| 250 ml 3% Acetone 97% Heptane | 14.8 | 2.3 | 79.4 | 3.5 | 38.23 |
| 250 ml 3% Acetone 97% Heptane | 1.7 | 1.4 | 77.9 | 19.0 | 25.15 |
| 250 ml 3% Acetone 97% Heptane | 0.1 | 0.3 | 40.5 | 59.1 | 17.20 |
| 500 ml 70% Acetone 30% Heptane | 1.7 | 0.2 | 15.2 | 83.0 | 10.39 |
| 500 ml Heptane | 2.1 | 2.1 | 8.5 | 7.3 | 5.91 |

Hence, by selective elution of the column, we were able to isolate fractions with γ-tocopherol content of 79.4% with 38.23% yield.

EXAMPLE 4

This example illustrates the effect of change in acetone concentration in elution of the product. 50 ml of FEED A was loaded onto the column by gravity flow as described in Example 1.

| Tocopherols (%) | Alpha | Beta | Gamma | Delta | Yield (%) |
|---|---|---|---|---|---|
| Raffinate | | | | | 0.00 |
| 500 ml Heptane | 98.6 | 0.1 | 1.0 | 0.3 | 4.72 |
| 250 ml 1.5% Acetone 98.5% Heptane | | | | | 0.00 |
| 250 ml 1.5% Acetone 98.5% Heptane | | | | | 0.00 |
| 250 ml 1.5% Acetone 98.5% Heptane | 1.3 | 1.7 | 86.9 | 10.1 | 31.30 |
| 250 ml 1.5% Acetone 98.5% Heptane | 2.1 | 0.3 | 35.6 | 62.0 | 32.92 |
| 500 ml 70% Acetone 30% Heptane | 0.2 | 0.3 | 17.6 | 82.0 | 20.37 |
| 500 ml Heptane | COLUMN REGENERATION | | | | |

Hence, by selective elution of the column, we were able to isolate fractions with γ-tocopherol content of 87% with 31.30% yield. Specifically, lowering the acetone concentration produced unexpectedly good results.

EXAMPLE 5

This example illustrates the effect of change in acetone concentration in elution of the product. 75 ml of FEED A was loaded onto the column by gravity flow as described in Example 1.

| Tocopherols (%) | Alpha | Beta | Gamma | Delta | Yield (%) |
|---|---|---|---|---|---|
| Raffinate | | | | | 0.00 |
| 500 ml Heptane | 16.4 | 1.8 | 69.8 | 12.0 | 37.75 |
| 100 ml 2% Acetone 98% Heptane | | | | | 0.00 |
| 100 ml 2% Acetone 98% Heptane | | | | | 0.00 |
| 100 ml 2% Acetone 98% Heptane | | | | | 0.00 |
| 100 ml 2% Acetone 98% Heptane | | | | | 0.00 |
| 100 ml 2% Acetone 98% Heptane | 4.5 | 1.7 | 76.2 | 17.6 | 19.23 |
| 250 ml 2% Acetone 98% Heptane | 1.9 | 1.3 | 66.6 | 30.2 | 20.61 |
| 250 ml 2% Acetone 98% Heptane | 0.3 | 0.4 | 44.0 | 55.2 | 4.21 |
| 500 ml 70% Acetone 30% Heptane | 0.3 | 1.5 | 14.0 | 84.3 | 6.39 |
| 500 ml Heptane | COLUMN REGENERATION | | | | |

Hence, by selective elution of the column, we were able to isolate fractions with γ-tocopherol content of 76.2% with 19.23% yield.

EXAMPLE 6

This example illustrates the separation of tocopherol homologues by strong base anion resins.

Preparation of Resin and Feed Material

A sample of commercially available, non-wintered, concentrated, and mixed tocopherols was obtained from ADM nutraceuticals, a division of Archer Daniels Midland Company, Decatur, Ill. The specifications of the product are given in Example 1.

A glass liquid-chromatography column (3.81 cm I.D.) was slurry packed in water with Mitsubishi Diaion PA408 resin obtained from Mitsubishi Industries America (Carmel, Ind.). PA408 is a Type II strong base anion with a dimethylethanolammonium group. The cross linkage is 4%. The resin was cleaned with 1 L deionized water. The resin was then back flushed with water. The resin bed expanded by about one-third of its original packed volume in order to partition the resin by size. The final packed volume was 280 ml. The resin was then flushed with 2 L of deionized water to remove all trace contaminants. The resin is sold in Cl— form. Consequently, to practice the embodiments of this invention, the ion type of the resin was converted to the OH— form by passing 2 L of 4% sodium hydroxide through the resin. The resin was then washed with deionized water until the washing solution became neutral. Then 1 L of anhydrous methanol (HPLC grade) was passed concurrently through the column in order to replace the water with the solvent.

Feed material for chromatographic separation using strong base anion resin was prepared by dissolving 100 g of Mixed Tocopherol Concentrate in 800 ml methanol (FEED B).

200 ml of FEED B was loaded on the resin column by gravity flow and the following fractions were eluted.

| Tocopherols (%) | Alpha | Beta | Gamma | Delta | Yield (%) |
|---|---|---|---|---|---|
| Raffinate | 0.00 | 0.00 | 0.00 | 100.00 | 3.13 |
| 500 ml 95% Methanol - 5% Acetone | 97.64 | 0.00 | 2.07 | 0.30 | 7.82 |
| 500 ml 95% Methanol - 5% Acetone | 85.05 | 0.34 | 14.58 | 0.03 | 3.33 |
| 500 ml 95% Methanol - 5% Acetone | 58.28 | 1.10 | 40.62 | 0.00 | 4.29 |
| 500 ml 95% Methanol - 5% Acetone | 28.45 | 1.67 | 69.76 | 0.12 | 4.73 |
| 500 ml 95% Methanol - 5% Acetone | 13.80 | 1.95 | 84.14 | 0.11 | 5.86 |
| 500 ml 95% Methanol - 5% Acetone | 6.04 | 2.20 | 91.68 | 0.07 | 6.66 |
| 500 ml 30% Methanol - 70% Acetone | 1.88 | 2.31 | 95.64 | 0.18 | 30.89 |
| 500 ml Methanol | 0.89 | 2.55 | 96.49 | 0.06 | 25.43 |

Hence, by selective elution of the column, we were able to isolate fractions with γ-tocopherol content of >95% with 56% yield.

EXAMPLE 7

This example illustrates the effect of change in acetone concentration in elution of the product. The column loaded with PA408 resin in Example 6 was regenerated by passing 1 L methanol. 200 ml of FEED B was subsequently loaded onto the column by gravity flow as described in Example 6.

| Tocopherols (%) | Alpha | Beta | Gamma | Delta | Yield (%) |
|---|---|---|---|---|---|
| Raffinate | 1.53 | 2.32 | 93.40 | 2.75 | 4.65 |
| 500 ml 93% Methanol - 7% Acetone | 2.84 | 2.27 | 92.21 | 2.68 | 13.93 |
| 500 ml 93% Methanol - 7% Acetone | 17.90 | 1.94 | 76.11 | 4.04 | 8.84 |
| 500 ml 93% Methanol - 7% Acetone | 27.52 | 2.75 | 66.28 | 3.46 | 9.82 |
| 500 ml 93% Methanol - 7% Acetone | 27.88 | 2.21 | 65.03 | 4.88 | 8.91 |
| 500 ml 93% Methanol - 7% Acetone | 19.00 | 2.14 | 71.66 | 7.21 | 4.55 |
| 500 ml 93% Methanol - 7% Acetone | 10.81 | 2.10 | 78.48 | 8.62 | 4.26 |
| 500 ml 30% Methanol - 70% Acetone | 4.24 | 2.02 | 86.05 | 7.69 | 18.09 |
| 500 ml Methanol | 1.25 | 2.18 | 88.87 | 7.69 | 26.95 |

Hence, by selective elution of the column, we were able to isolate fractions with γ-tocopherol content of >86% with 45% yield.

EXAMPLE 8

This example illustrates the effect of change in acetone concentration in elution of the product. The column loaded with PA408 resin in Example 6 was regenerated by passing 1 L methanol. 200 ml of FEED B was subsequently loaded onto the column by gravity flow as described in Example 6.

| Tocopherols (%) | Alpha | Beta | Gamma | Delta | Yield (%) |
|---|---|---|---|---|---|
| Raffinate | 0.54 | 2.57 | 94.38 | 2.51 | 4.94 |
| 500 ml 97% Methanol - 3% Acetone | 8.47 | 2.68 | 88.42 | 0.43 | 12.77 |
| 500 ml 97% Methanol - 3% Acetone | 48.28 | 1.59 | 49.10 | 1.03 | 7.98 |
| 500 ml 97% Methanol - 3% Acetone | 59.47 | 1.14 | 37.61 | 1.78 | 6.56 |
| 500 ml 97% Methanol - 3% Acetone | 43.41 | 1.35 | 52.62 | 2.63 | 5.42 |
| 500 ml 97% Methanol - 3% Acetone | 23.04 | 1.65 | 72.43 | 2.87 | 5.45 |
| 500 ml 97% Methanol - 3% Acetone | 11.81 | 1.90 | 81.87 | 4.43 | 6.37 |
| 500 ml 30% Methanol - 70% Acetone | 4.51 | 1.97 | 90.61 | 2.90 | 29.49 |
| 500 ml Methanol | 1.89 | 2.19 | 92.66 | 3.25 | 21.03 |

Hence, by selective elution of the column, we were able to isolate fractions with γ-tocopherol content of >90% with 50% yield.

EXAMPLE 9

This example compares the different acidic elution steps from prior art (U.S. Pat. Nos. 3,122,56, 3,402,182 and 5,487,817). The column loaded with PA408 resin in Example 6 was regenerated by passing 1 L methanol. 200 ml of FEED B was subsequently loaded on to the column by gravity flow as described in Example 6.

| Tocopherols (%) | Alpha | Beta | Gamma | Delta | Yield (%) |
|---|---|---|---|---|---|
| Raffinate | 2.62 | 1.23 | 61.93 | 34.21 | 8.11 |
| 500 ml Methanol | 0.00 | 0.00 | 50.00 | 50.00 | 7.51 |
| 500 ml Methanol | 94.39 | 0.00 | 5.61 | 0.00 | 3.67 |
| 500 ml Methanol | 70.44 | 0.40 | 29.16 | 0.00 | 10.51 |
| 500 ml 95% Methanol - 5% Acetone | 13.32 | 1.53 | 68.29 | 16.86 | 5.14 |
| 500 ml 95% Methanol - 5% Acetone | 10.77 | 1.87 | 85.46 | 1.90 | 5.81 |
| 500 ml 99% Methanol - 1% Water | 4.20 | 2.05 | 91.63 | 2.12 | 6.04 |
| 500 ml 95% Methanol - 5% Acetic Acid | 2.11 | 2.27 | 95.56 | 0.06 | 53.20 |

By using the procedures described in prior art, we are able to isolate fractions with γ-tocopherol content of >90% with 60% yield. However, the column used in this procedure needs to be regenerated with alkali solution followed by washing with water to remove excess alkali solution and removal of water with methanol. This invention avoids all of these steps and allows easy manufacture of high purity tocopherols.

EXAMPLE 10

Another strong base anion resin, Dowex MSA2 was obtained from Dow Chemical Company, Midland, Mich. and load onto a glass chromatography column (3.81 cm ID) using the procedure described in Example 6. The final packed volume was 280 ml. The resin was converted to OH— by passing 2 L 4% sodium hydroxide followed by washing with water until the passing solution becomes neutral. HPLC grade methanol was then passed concurrently through the column to replace water.

Feed material for chromatographic separation using strong base anion resin was prepared by dissolving 50 g mixed tocopherol concentrate in 400 ml methanol (FEED C). 200 ml of FEED C was loaded on to the column by gravity flow and the following fractions were elected.

| Tocopherols (%) | Alpha | Beta | Gamma | Delta | Yield (%) |
|---|---|---|---|---|---|
| Raffinate | 63.13 | 0.60 | 29.02 | 7.26 | 1.51 |
| 500 ml 95% Methanol - 5% Acetone | 18.28 | 1.74 | 75.11 | 4.87 | 35.80 |
| 500 ml 95% Methanol - 5% Acetone | 6.58 | 2.05 | 82.57 | 8.79 | 11.32 |
| 500 ml 95% Methanol - 5% Acetone | 2.01 | 2.02 | 77.06 | 18.91 | 4.98 |
| 500 ml 95% Methanol - 5% Acetone | 1.76 | 1.79 | 61.35 | 35.10 | 3.40 |
| 500 ml 95% Methanol - 5% Acetone | 0.38 | 1.54 | 44.48 | 53.59 | 2.49 |
| 500 ml 95% Methanol - 5% Acetone | 0.33 | 1.25 | 29.97 | 68.45 | 1.82 |
| 500 ml 30% Methanol - 70% Acetone | 0.20 | 0.88 | 26.81 | 72.11 | 26.09 |
| 500 ml Methanol | 0.28 | 0.42 | 8.11 | 91.19 | 12.59 |

Hence, by using the procedure described in the embodiments of this invention, we are able to isolate fractions containing >80% γ-tocopherol and >90% δ-tocopherol.

EXAMPLE 11

The resin used in Example 10 was regenerated by passing 1 L methanol. 200 ml of FEED C was loaded onto the column by gravity flow and the following fractions were eluted.

| Tocopherols (%) | Alpha | Beta | Gamma | Delta | Yield (%) |
|---|---|---|---|---|---|
| Raffinate | 12.96 | 1.67 | 69.57 | 15.79 | 43.16 |
| 500 ml Methanol | 32.88 | 4.47 | 18.08 | 44.57 | 27.29 |
| 500 ml Methanol | 11.02 | 2.05 | 71.41 | 15.53 | 9.27 |
| 500 ml Methanol | 3.59 | 2.09 | 71.41 | 22.91 | 6.18 |
| 500 ml 95% Methanol - 5% Acetone | 0.67 | 2.10 | 54.90 | 42.33 | 4.00 |
| 500 ml Methanol - 5% Acetone | 0.10 | 1.26 | 25.49 | 73.14 | 1.69 |
| 500 ml 99% Methanol - 1% Water | 0.00 | 0.69 | 9.80 | 89.51 | 0.87 |
| 500 ml 95% Methanol - 5% Acetic Acid | 0.06 | 0.17 | 1.37 | 98.40 | 12.20 |

By using the procedures described in prior art, we are able to isolate fractions with δ-tocopherol content of >98% with 12% yield. However, the column used in this procedure needs to be regenerated with alkali solution followed by washing with water to remove excess alkali solution and removal of water with methanol. This invention avoids all these steps and allows easy manufacture of high purity tocopherols.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

Having now fully described this invention, it will be understood to those of ordinary skill in the art that the same can be performed within a wide and equivalent range of conditions, formulations, and other parameters without affecting the scope of the invention or any embodiment thereof.

What is claimed is:

1. A process for separating a tocopherol homologue mixture from tocopherol containing materials, said process comprising,
    a. dissolving a tocopherol containing material in a non-polar organic solvent,
    b. contacting the dissolved material with a non-ionic adsorbent resin,
    c. eluting adsorbed tocopherol homologues by passing a mixture of said non-polar organic solvent and a polar solvent through said resin, and
    d. collecting a tocopherol homologue mixture from the eluate.

2. The process of claim 1 wherein said non-ionic adsorbent resin is a resin consisting essentially of silica.

3. The process of claim 1 wherein said tocopherol homologue mixture is a mixture comprising above about 80% γ-tocopherol.

4. A process for preparing a tocopherol homologue mixture from tocopherol containing materials, said process comprising,
    a. dissolving a tocopherol containing material in a first polar solvent,
    b. contacting the dissolved material with a strong basic anion resin, said resin being in the hydroxyl form,
    c. eluting adsorbed tocopherol homologues by passing a mixture of the first polar solvent and a second polar solvent through said resin, and
    d. collecting a tocopherol homologue mixture form the eluate.

5. The process of claim 4 wherein said strong basic anion resin is porous.

6. The process of claim 4 wherein said tocopherol homologue mixture is a mixture comprising above about 90% γ-tocopherol.

7. A process for isolating tocopherol homologues from a tocopherol homologue mixture, said process comprising,
    a. contacting a tocopherol homologue mixture dissolved in a non-polar solvent with a non-ionic adsorbent resin immersed in said non-polar solvent,
    b. passing a non-polar solvent mixed with a polar solvent through said resin containing adsorbed tocopherol homologue mixture,
    c. collecting the eluate in fractions, and
    d. obtaining isolated tocopherol homologues from said fractions.

8. A process for isolating tocopherol homologues from a tocopherol homologue mixture, said process comprising,
    a. contacting a tocopherol homologue mixture dissolved in a first polar solvent with a strong basic anion resin immersed in said first polar solvent, said resin being in the hydroxyl form,
    b. passing said first polar solvent mixed with a second polar solvent through said resin containing adsorbed tocopherol homologue mixture,
    c. collecting the eluate in fractions, and
    d. obtaining isolated tocopherol homologues from said fractions.

9. The process of claim 8 wherein said first polar solvent is methanol.

10. The process of claim 8 wherein said second polar solvent is acetone.

* * * * *